(12) United States Patent
Steinman et al.

(10) Patent No.: US 9,357,766 B2
(45) Date of Patent: Jun. 7, 2016

(54) ORGAN TRANSPORT APPARATUS WITH A DOCUMENT COMPARTMENT AND A TAMPER EVIDENT SEAL

(75) Inventors: Christopher P. Steinman, Sandy, UT (US); Robert J. Allen, Crystal Lake, IL (US); David Pettinato, Schaumburg, IL (US); Matthew Copithorne, Framingham, MA (US); Brian L. Otts, Warrior, AL (US); Peter Demuylder, Londerzeel (BE)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 372 days.

(21) Appl. No.: 13/545,184

(22) Filed: Jul. 10, 2012

(65) Prior Publication Data

US 2014/0017659 A1    Jan. 16, 2014

(51) Int. Cl.
*A01N 1/02* (2006.01)

(52) U.S. Cl.
CPC ............ *A01N 1/0247* (2013.01); *A01N 1/0273* (2013.01)

(58) Field of Classification Search
None
See application file for complete search history.

(56) References Cited

U.S. PATENT DOCUMENTS

| | | | |
|---|---|---|---|
| 4,502,295 A | 3/1985 | Toledo-Pereyra | |
| 4,745,759 A | 5/1988 | Bauer et al. | |
| 5,157,930 A | 10/1992 | McGhee et al. | |
| 5,285,657 A | 2/1994 | Bacchi et al. | |
| 5,356,771 A | 10/1994 | O'Dell | |
| 5,391,136 A * | 2/1995 | Makowka | 493/210 |
| 5,441,170 A | 8/1995 | Bane, III | |
| 5,586,438 A | 12/1996 | Fahy | |
| 6,673,594 B1 * | 1/2004 | Owen et al. | 435/284.1 |
| 7,278,270 B2 | 10/2007 | Culp et al. | |
| 7,749,693 B2 | 7/2010 | Brassil et al. | |
| 2004/0050849 A1 * | 3/2004 | Pickles | 220/324 |
| 2006/0208881 A1 | 9/2006 | Suzuki | |
| 2007/0048725 A1 | 3/2007 | Arrington | |
| 2008/0219885 A1 * | 9/2008 | Horstman | 422/61 |
| 2010/0304352 A1 | 12/2010 | Patrick, III et al. | |
| 2011/0076666 A1 | 3/2011 | Brassil | |

(Continued)

FOREIGN PATENT DOCUMENTS

| | | |
|---|---|---|
| EP | 0 475 144 A2 | 3/1992 |
| EP | 1 688 124 A1 | 8/2006 |

(Continued)

OTHER PUBLICATIONS

Barcode Sticker: http://www.google.com/url?sa=t&rct=j&q=&esrc=s&frm=1&source=web&cd=1&ved=0CCMQFjAA&url=http%3A%2F%2Fwww.usdtl.com%2F_literature_96108%2FTamper_evident_requisition_form_barcode_sticker_article&ei=F_OJVPf5NqHIsQSx1ILoDw&usg=AFQjCNF7o0yO9xxbaJ82rvmnvPWU93Srmw&bvm=bv.81456516,d.cWc ; posted online Dec. 11, 2007.*

(Continued)

*Primary Examiner* — Jill Warden
*Assistant Examiner* — Benjamin Whatley
(74) *Attorney, Agent, or Firm* — Oliff PLC (57) ABSTRACT

A perfusion apparatus including a perfusion circuit that perfuses an organ or tissue has a compartment that supports an organ or tissue during perfusion, an internal cover, and an external cover that closes the apparatus. A wall portion may extend substantially perpendicularly between the internal cover and the external cover to define a document compartment between the internal cover, the external cover and the wall portion. A tamper evident seal will not permit the external cover to open without creating a record of whether the external cover has been opened after the tamper evident seal has been activated.

24 Claims, 6 Drawing Sheets

(56) References Cited

U.S. PATENT DOCUMENTS

| | | | |
|---|---|---|---|
| 2011/0129908 A1 | 6/2011 | Owen et al. | |
| 2011/0136096 A1 | 6/2011 | Hassanein et al. | |
| 2011/0173023 A1* | 7/2011 | LeClair et al. | 705/2 |
| 2012/0276620 A1* | 11/2012 | Kravitz et al. | 435/284.1 |
| 2013/0177897 A1* | 7/2013 | Kravitz et al. | 435/1.2 |

FOREIGN PATENT DOCUMENTS

| | | | |
|---|---|---|---|
| EP | 1688124 A1 * | 8/2006 | |
| WO | WO 03/030769 A2 | 4/2003 | |
| WO | WO 2004/089235 A2 | 10/2004 | |
| WO | WO 2009/041806 A1 | 4/2009 | |
| WO | WO 2012/125782 A2 | 9/2012 | |
| WO | WO 2012/148690 A1 | 11/2012 | |
| WO | WO 2013/106248 A2 | 7/2013 | |

OTHER PUBLICATIONS

Locking container loops: http://web.archive.org/web/20110524000451/http://reusabletranspack.com/templates/insulated%20containers/PB09%20POP%20%20Insulated%20Containers.html.*

Feb. 14, 2014 International Search Report issued in International Patent Application No. PCT/US2013/049584.

Feb. 14, 2014 Written Opinion of the International Searching Authority issued in International Patent Application No. PCT/US2013/049584.

Patrick, Charles, "Waters Advanced Viability Evaluation System WAVES," Jun. 2009, pp. 1-12, IGL Group, USA.

Aug. 11, 2009 Picture of Waters WAVES device taken from a trade show in France.

Kravitz et al., U.S. Appl. No. 13/545,210, filed Jul. 10, 2012.

Aug. 28, 2014 Office Action issued in U.S. Appl. No. 13/545,210.

Mar. 28, 2014 Written Opinion of the International Searching Authority issued in International Patent Application No. PCT/US2013/049580.

Mar. 28, 2014 International Search Report issued in International Patent Application No. PCT/US2013/049580.

Anonymous, "SaBTO: Guidance on the Microbiological Safety of Human Organs, Tissues and Cells Used in Transplantation," The Advisory Committee on the Safety of Blood, Tissues and Organs, Feb. 21, 2011, pp. 1-60.

Anonymous, "Guidance for Industry: Eligibility Determination for Donors of Human Cells, Tissues and Cellular and Tissue-Based Products (HCT/Ps)," U.S. Department of Health and Human Services, Aug. 1, 2007, pp. 1-70.

Anonymous, "LifePort Kidney Transporter Operator's Manual," Organ Recovery Systems, Jul. 21, 2007.

Mar. 13, 2015 Office Action in corresponding U.S. Appl. No. 13/545,210.

Salvalaggio et al, "Crossmatch Testing in Kidney Transplantation: Patterns of Practice and Associations with Rejection and Graft Survival", Saudi J Kidney Dis Transpl. Jul. 2009; 20(4): 577-589.

Demetris et al, "A clinicopathological Study of Human Liver Allograft Recipients Harboring Preformed IgG Lymphocytotoxic Antibodies", Hepatology, Sep. 1992; 16(3): 671-681.

Singh et al, "Positive, Warm T cell crossmatch in cardiac transplantation: with transient vasculitis and without hyperacute rejection", Transplantation, May 1982; 33(5): 564-566.

Strobel, E., "Hemolytic Transfusion Reactions", Transfus Med Hemother. 2008; 35: 346-353.

World Health Organization (WHO), "Manual on the management, maintenance and use of blood cold chain equipment", Published 2005; pp. 1-92, ISBN 9241546735.

Dec. 3, 2015 Office Action issued in U.S. Appl. No. 13/545,210.

* cited by examiner

ORGAN TRANSPORT APPARATUS WITH A DOCUMENT COMPARTMENT AND A TAMPER EVIDENT SEAL

BACKGROUND

Documents such as medical records may be used for a variety of reasons in conjunction with an organ or tissue that is being stored, transported, assessed and/or treated in perfusion apparatus. Typically, these documents are transported at the same time as the organ or tissue and are transported separately and/or are externally accessible. Additionally, the apparatus used to transport the organ or tissue and the apparatus used to transport the documents can be freely opened during transport.

The practice of storing and protecting an organ or tissue and related documents as discussed above suffers certain shortfalls. If documents are altered or unavailable, a doctor or clinician may refuse to use an organ or tissue because necessary information may be unavailable or may be of questionable authenticity.

An apparatus has been disclosed in which documents are transported in an external compartment of the apparatus, and can be accessed when the apparatus is closed. See U.S. Pat. No. 6,673,594 to Owen et al. However, external access to documents increases the likelihood of unauthorized alteration of the information contained in the documents or loss of the documents. An organ or tissue container that is opened during storage or transport may be contaminated, and the organ or tissue may be exposed to environmental conditions that are detrimental to the viability and health of the organ or tissue. These problems may jeopardize the health of the organ or tissue and the ultimate success of the procedure in which the organ or tissue is to be used.

SUMMARY

For convenience, as used herein, the term organ is intended to encompass both an organ and/or tissue, unless otherwise stated. A perfusion device may include an internal document compartment and/or may provide a tamper evident closure. Such a device may reduce cost, conserve space, provide convenience, and increase security to the organ and associated documents. The device carrying the organ and the documents may provide improved convenience because the organ and the documents are both internally accessible within the same device. As a result, the device minimizes the likelihood of the documents and the organ being separated from each other or separately accessed. The documents for the organ stay together with the organ in the same device to ensure that the doctor or clinician using the organ receives suitable organ information for use, such as for transplantation, assessment and/or testing. Since the documents are located internal to the device, the documents are not externally accessible. This may avoid unauthorized alterations to the information in the documents and reduce likelihood of loss. As a result, the device provides increased security to the documents and the organ during transport.

The device may include one or more tamper evident closures to protect the organ, documents and/or the perfusion circuit. The tamper evident closure may alert a user that the device has been opened at an unauthorized time and/or location and/or by an unauthorized person. Also, based on this information, a doctor or clinician can make an appropriate diagnosis prior to conducting further testing to determine whether the organ is still acceptable for use. Thus, the tamper evident closure may mitigate risks that jeopardize the health of the organ and the ultimate success of the procedure in which the organ is used. Tamper evident closures may be provided on any feature that can be opened. Preferably, tamper evident closures are provided on lids or covers to indicate whether the lids or covers have been opened.

BRIEF DESCRIPTION OF THE DRAWINGS

Exemplary implementations can be described with reference to the following figures wherein.

DETAILED DESCRIPTION OF EMBODIMENTS

Exemplary implementations include a perfusion apparatus having a perfusion circuit configured to perfuse an organ or tissue, a compartment in which the organ or tissue may be supported during perfusion by the perfusion apparatus, an internal cover that may be configured to close the compartment, a first external cover configured to close the perfusion apparatus and a wall portion extending substantially perpendicularly from the internal cover toward the first external cover to define a document compartment between the internal cover, the first external cover and the wall portion. The perfusion circuit may be configured such that a bottom surface of the first external cover may be adjacent to a top surface of the wall portion to substantially enclose the document compartment. The wall portion preferably includes four wall portions that define a rectangular document compartment, wherein internal dimensions of the document compartment may be large enough to incorporate standard size documents such as A4, 8½×11" or 8½×13" documents. For example, the document compartment may be at least 0.1×9×12 inches. Preferably, the document compartment may be at least 0.5×9×12 inches. More preferably, the document compartment may be at least 0.9×9.8×12.3 inches. The perfusion apparatus may also include a second external cover configured to close the perfusion apparatus in cooperation with the first external cover, and arranged such that the document compartment is not open when the first external cover is closed, whether or not the second external cover is open or closed.

Exemplary implementations may include an apparatus for at least one of perfusion, storage, assessment, treatment and transport of an organ or tissue. The apparatus may include a perfusion circuit configured to perfuse the organ or tissue, a first external cover configured to close the apparatus, and a first tamper evident seal. The first tamper evident seal may be located at a surface of the first external cover and at a surface that is not part of the first external cover in an initial state while the first external cover is in a closed position and at a location that will not permit the first external cover to open without changing the initial state of the first tamper evident seal. The first tamper evident seal indicates whether the first external cover has been opened after the first tamper evident seal has been activated. The apparatus may include a compartment in which the organ or tissue may be supported during perfusion by the apparatus, an internal cover that may be configured to close the compartment and a second tamper evident seal. The second tamper evident seal may be located at a surface of the internal cover and at a surface that is not part of the internal cover in an initial state while the internal cover is in a closed position and at a location that will not permit the internal cover to open without changing the initial state of the second tamper evident seal. The second tamper evident seal indicates whether the internal cover has been opened after the second tamper evident seal has been activated. The apparatus may include a second external cover configured to close the apparatus in cooperation with the first external cover, and a third tamper evident seal. The third tamper evident seal may be located at a surface of the second external cover and at a surface that is not part of the second external cover in an initial state while the second external cover is in a closed position and at a location that will not permit the second external cover to open without changing the initial state of the third tamper evident seal. The third tamper evident seal indicates whether the second external cover has been opened after the third tamper evident seal has been activated.

Exemplary implementations may include a method of storing and/or transporting an organ or tissue and an associated document. The method may include placing the organ or tissue in a compartment in a perfusion apparatus having a first external cover configured to close the perfusion apparatus and placing the document in the perfusion apparatus in a location that is under the first external cover when the first external cover is closed. The first external cover may then be closed, and the perfusion apparatus containing the organ or tissue and the document may be stored or transported without opening the first external cover.

Exemplary implementations may include a method of securely storing and/or transporting an organ or tissue in a perfusion apparatus. The method may include activating an internal tamper-evident seal after placing the organ or tissue in the compartment in the perfusion apparatus and closing the compartment with an internal cover, wherein the internal tamper-evident seal indicates whether or not the internal cover has been opened after the internal tamper-evident seal has been activated. The method may include activating a first external tamper-evident seal after placing the document in the perfusion apparatus and closing the first external cover, wherein the first external tamper-evident seal indicates whether or not the first external cover has been opened after the first external tamper-evident seal has been activated. The method may include closing the perfusion apparatus with a second external cover in cooperation with the first external cover and activating a second external tamper-evident seal after closing the second external cover, wherein the second external tamper-evident seal indicates whether or not the second external cover has been opened after the second external tamper-evident seal has been activated. After the tamper evident seal(s) is activated, the method may further include storing or transporting the perfusion apparatus containing the organ or tissue and thereafter checking the tamper evident seal(s) to determine whether or not the respective cover(s) has been opened.

These and other features and advantages of the disclosed apparatus and method are described in, or apparent from, the following detailed description of various exemplary implementations.

The following exemplary embodiments may refer to a perfusion apparatus, transport apparatus, and/or storage apparatus for an organ having a document compartment and/or one or more tamper evident closures. It should be appreciated that, although the exemplary embodiments according to this disclosure may be applicable to specific applications, the depictions and/or descriptions included in this disclosure are not intended to be limited to any specific application.

A document compartment 160 may carry a plurality of similar or different types of documents, such as medical records, medical charts, donor information, organ and/or biological sample data. It may be advantageous to safely store these documents and an organ together in a same apparatus. If the documents for an organ are lost, then the doctor or clinician may refuse to use the organ and/or any results associated with the organ. This is because any procedure using the organ may require organ data to ensure, for example, compatibility of the organ to the recipient, chain of custody to ensure that the organ or any of the associated documents have not been tampered with during transport, identity of the organ and/or biological sample to ensure that the organ is the organ requested and/or viability of the organ and/or biological sample to ensure that the organ and/or biological sample are healthy, stable and prepared for use. If the documents for the biological samples are lost or cannot be correlated to the organ, the results from any testing of the biological samples may not be used or useful because the original state of the biological samples and their relationship to the organ is uncertain.

Figure 1:
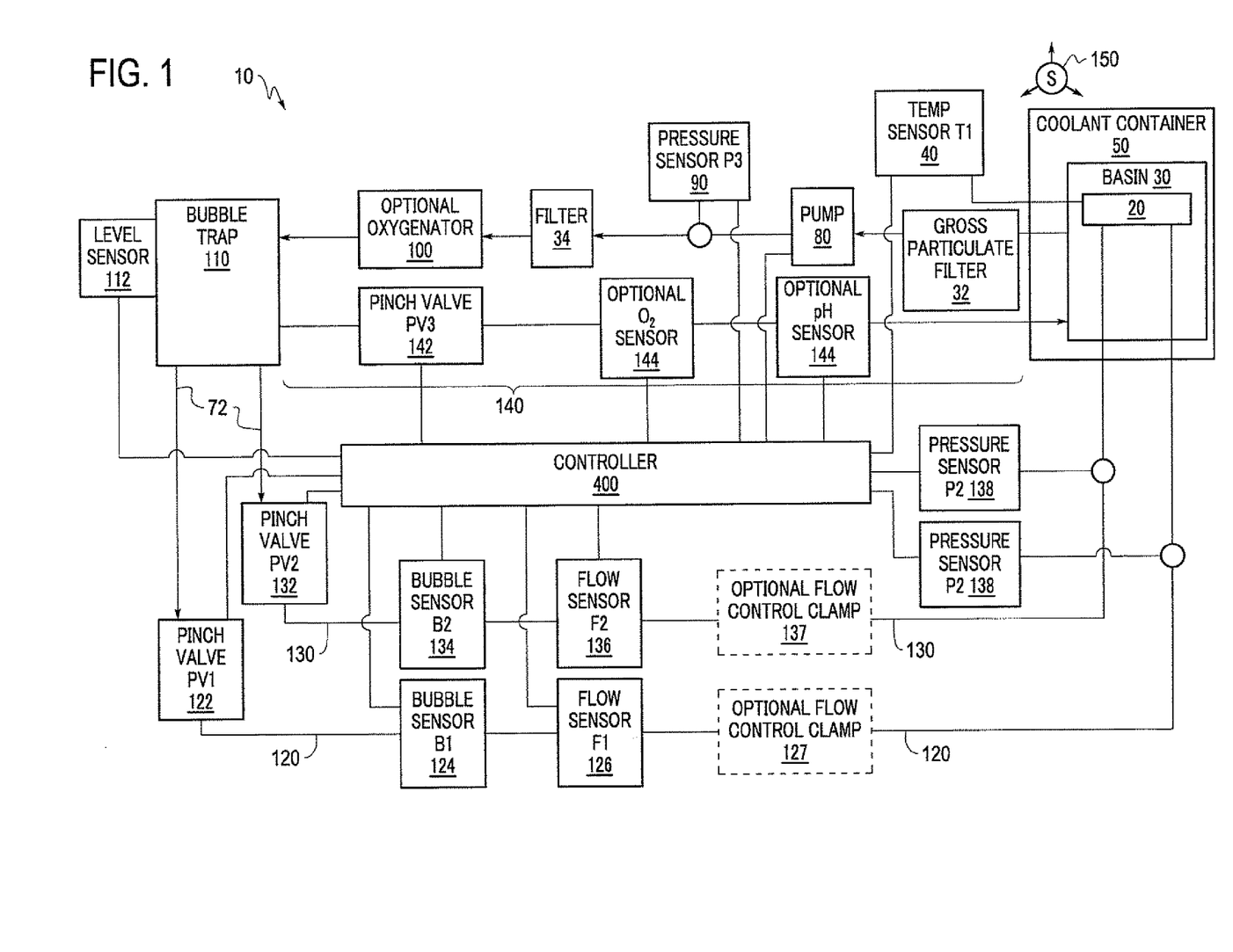
FIG. 1 illustrates a schematic diagram of a perfusion apparatus, transport apparatus, and/or storage apparatus for an organ.
Figure 4:
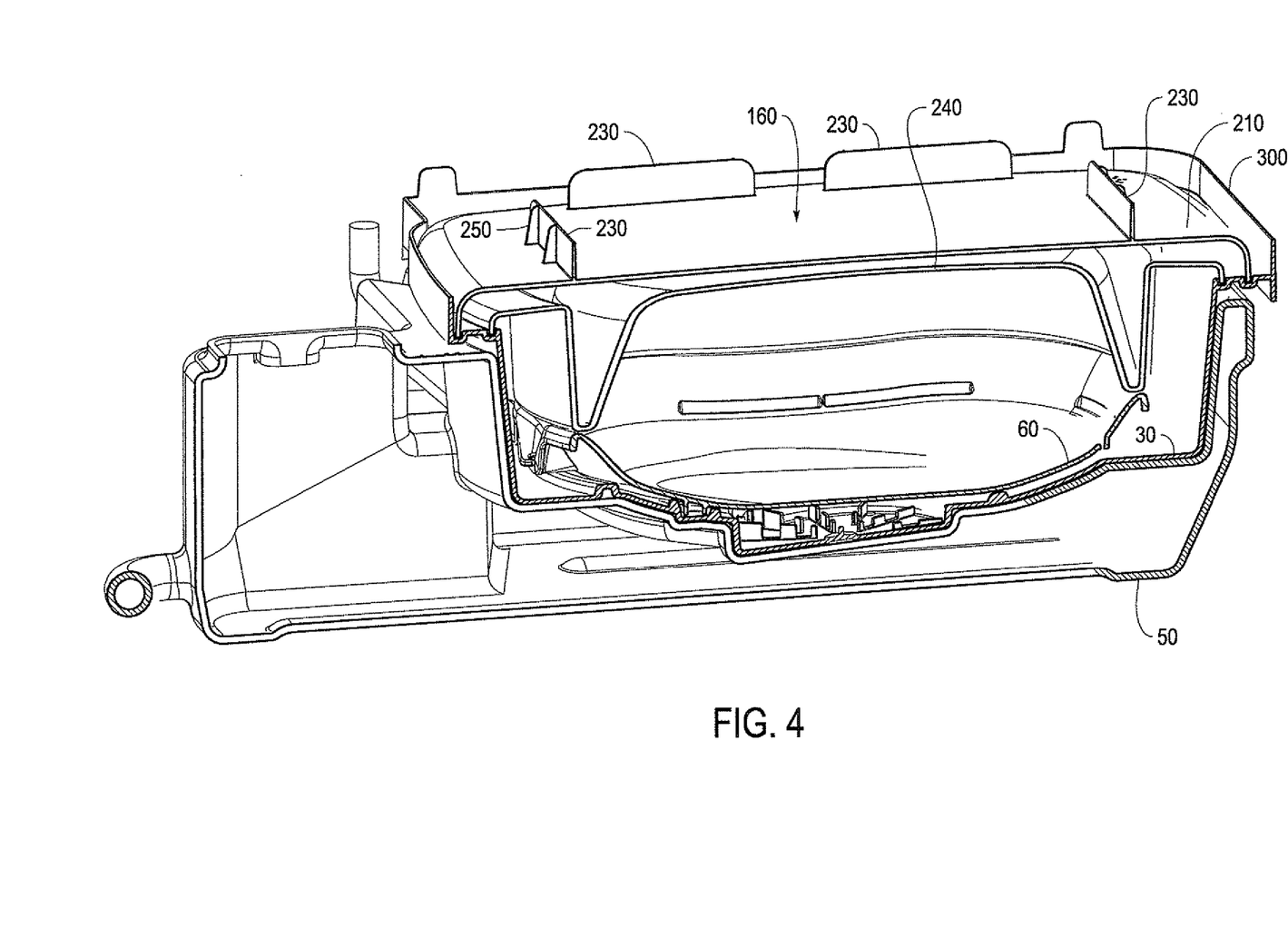
FIG. 4 illustrates an exemplary cross-sectional perspective view, taken along the line 4-4 in FIG. 3, of an internal compartment of the apparatus.

FIG. 1 is a schematic diagram of a perfusion apparatus, transport apparatus, and/or storage apparatus 10 for an organ 20. The organ 20 may preferably be a liver but may be any human or animal, natural or engineered, healthy, injured or diseased organ or tissue. The apparatus includes a basin 30 in which the organ may be placed. The basin 30 may hold a cradle 60 as illustrated in FIG. 4, which preferably includes a surface on which the organ 20 is disposed when the organ 20 is in the apparatus 10. The basin 30 may include a first filter that can function as a gross particulate filter. The basin 30 and/or the cradle 60 are preferably configured to allow a perfusate bath to form around the organ 20. The basin 30 and/or apparatus 10 may also include one or more temperature sensor 40 located in or near the cradle 60. The basin may include multiple temperature sensors 40, which may provide redundancy in the event of a failure and/or may provide temperature measurement at multiple locations. Preferably, the temperature sensor 40 is an infrared temperature sensor. The temperature sensor(s) 40 is preferably disposed as close as practical to the organ 20 when the organ 20 is disposed in the cradle 60 in order to improve the usefulness and accuracy of the temperature sensor(s) 40, which preferably provides a temperature measurement of the perfusate that may be correlated to a temperature of the organ 20. Alternatively or additionally, the temperature sensor(s) 40 may be used to directly measure the temperature of the organ 20.

The basin 30 is preferably disposed within a cooling container 50 that may contain cold materials such as ice, ice water, brine or the like. Cooling container 50 may be permanently or removably attached to, or an integral, monolithic part of, apparatus 10. Thus, in use, the organ 20 is disposed within the cradle 60, which is disposed within the basin 30, which is disposed within the cooling container 50. Preferably, each of the basin 30, cradle 60 and cooling container 50 is configured, or keyed, to fit within its corresponding mating component in a single orientation. The configuration of the cooling container 50, basin 30 and cradle 60 may provide a configuration that provides cooling for the organ 20 without the contents of cooling container 50 contacting the organ 20 or the cradle 60. Although the cooling container 50 is described herein as containing ice or ice water, any suitable cooling medium can be used. Ice may be preferable due to the ease with which ice can be procured, but one of ordinary skill would understand that any suitable cooling medium, which could be an active cooling medium (such as a thermo electric cooler or a refrigerant loop) or a passive cooling medium similar to ice or ice water, or a combination thereof, may be utilized. The amount of ice, or other cooling medium, that can be placed within the cooling container 50 should be determined based upon the maximum time that cooling is to be provided while the organ 20 will be in the apparatus 10.

The cradle 60 may include components configured to securely restrain the organ 20 in place. Such components may, for example, include user selectable netting that is fastened to the cradle 60.

After passing through the filter 32, the perfusate flows along a first flow path 70 that includes a suitable fluid conduit 72, such as flexible or rigid tubing, a pump 80, a pressure sensor 90, a second filter 34, an optional oxygenator 100 and a bubble trap 110, each of which is discussed below.

The first filter 32 is preferably a relatively coarse filter (relative to the second filter 34). Such a coarse filter may be provided to prevent large particles, which may for example be byproducts of the organ or of the organ being removed from the donor, from entering and clogging fluid paths of the apparatus 10. The first filter 32 may be an integral part of the basin 30 or the first filter may be disposed elsewhere in the first flow path 70 downstream of the basin 30. The first filter 32 may also be a separate component from the basin 30 or disposed within the fluid conduit 72.

The first flow path 70 may also include a pump 80. The pump 80 may be any pump that is suitable in connection with perfusing of organs. Examples of suitable pumps may include hand-operated or electric pumps, such as centrifugal pumps and roller pumps. If a roller pump is included, the roller pump may include a single channel or flow path (where only one tube is compressed by the rollers) or the roller pump may include multiple, parallel channels or flow paths (where multiple tubes are compressed by the rollers). If multiple, parallel channels or flow paths are included, the rollers may preferably be disposed out of phase or offset so that pulses created by the rollers are out of phase, which may result in a fluid flow out of the roller pump that is relatively less pulsatile than would be the case with a single roller. Such a multiple channel roller pump may achieve a constant flow rate or a minimally pulsatile flow rate, which may be advantageous depending on the other components in the flow path and/or the type of organ being perfused.

The flow path 70 may include a pressure sensor 90. The pressure sensor 90 may be preferably disposed after the outlet of the pump 80 in order to monitor and/or be used to control the pressure produced at the outlet of the pump by way of a suitable controller. The pressure sensor 90 may provide continuous or periodic monitoring of pressure.

The flow path 70 may include an oxygenator 100 such as an oxygenator membrane or body to provide oxygenation to the perfusate. Oxygen may be provided to the oxygenator 100 by any suitable means. Suitable oxygen sources may include pure oxygen or mixed gases such as air. The gas may be compressed, such as in a high-pressure cylinder, liquefied as would be stored in a dewar, or drawn from the surrounding atmosphere. Preferably, the oxygen may be provided by way of an oxygen generator, which may be separate from the apparatus 10 or integral to the apparatus 10. Oxygen may be generated through any suitable means, some examples of which include through pressure swing adsorption using a molecular sieve, through a ceramic oxygen generator (a solid state oxygen pump) or through decomposition of water.

The flow path 70 may include a bubble trap 110. The bubble trap 110 preferably separates gas bubbles that may be entrained in the perfusate flow and prevents such bubbles from continuing downstream and entering the organ 20. The bubble trap 110 may also function as an accumulator that reduces or eliminates pulsatility of the perfusate flow. The bubble trap 110 may include a volume of gas, initially or through the accumulation of bubbles, such that pressure fluctuations in the perfusate are dampened or eliminated.

The bubble trap 110 may include a vent that allows purging of gas during start up or a purging process. The vent may be connected to or part of purge flow path 140. The vent is preferably open during a start up process so that any air or other gas may be purged from the perfusate path 70. When the vent is open, valves 122, 132 will preferably both be closed. Once the gas is purged from the perfusate path 70, the vent may preferably be closeable. The vent may be closed manually or may be closed automatically by way of a suitable controller.

The bubble trap 110 may include a level sensor 112. A level sensor 112 may optionally be used during the purging process to determine when the purging is complete and/or may be used to determine when the purging process needs to be repeated, which may happen after gas has been trapped in the bubble trap 110. Also, through use of the level sensor 112 and the vent, the accumulator function of the bubble trap can be tuned to account for differing amplitudes and frequencies of pulsatility in the perfusate flow. The accumulator function of the bubble trap may be tuned, for example, by adjusting the volumetric ratio of air to perfusate fluid.

The bubble trap 110 may have any number of outlets, as needed for a given application of the perfusion apparatus. In FIG. 1, three outlets are shown connected to three different flow paths, which may be particularly suited for the perfusion of a liver. When perfusing a liver, the three paths preferably include portal flow path 120 connected to the portal vein of a liver, hepatic flow path 130 connected to the hepatic artery of a liver, and bypass flow path 140 that provides a return path to the basin 30. There may also be a port in any fluid path that allows access to the perfusate solution. The port may preferably be located in the bubble trap 110. This port may preferably include a luer type fitting such that a user may extract a sample of the perfusate for analysis. The port may also be utilized by a user to administer drugs to the perfusate without opening the basin.

As shown in FIG. 1, the portal flow path 120 and hepatic flow path 130 may optionally include similar or different components such as valves 122, 132; bubble sensors 124, 134; flow sensors 126, 136; flow control clamps 127, 137; and pressure sensors 128, 138. Each similar component may function in a similar manner, and such pairs of components may optionally be structurally and/or functionally identical to reduce manufacturing costs. Flow sensors 126, 136 may preferably be ultrasonic sensors disposed around tubing, although any suitable sensor may be used. Ultrasonic sensors may be advantageous because in normal usage such sensors do not come into contact with the perfusate and therefore are not in the sterile path. Such an implementation of ultrasonic sensors does not require replacement and/or cleaning after use.

Valves 122, 132 may be pinch valves that function to squeeze tubing and reduce or shut off flow, but any suitable valve may be used. Pinch valves may be advantageous because in normal usage they do not come into contact with the perfusate and therefore do not require replacement and/or cleaning after use.

Preferably, the bubble sensors 124, 134 are ultrasonic sensors disposed around tubing, although any suitable sensor may be used. Similar to pinch valves, ultrasonic sensors may be advantageous because in normal usage they do not come into contact with the perfusate and therefore do not require replacement and/or cleaning after use. Instead, ultrasonic sensors can be disposed in contact with, adjacent to or around an external surface of tubing in order to sense bubbles.

Flow control clamps 127, 137 may be used to fine-tune the flow rate in one or both of portal flow path 120 and hepatic flow path 130. Preferably, the organ provides self-regulation to control flow that exits the bubble trap 110 and is divided between the portal flow path 120 and the hepatic flow path 130. In such self-regulated flow, pressure sensors 128, 138 provide overpressure monitoring. In the event that pressure delivered to the organ in either or both of the portal flow path 120 or the hepatic flow path 130 exceeds a predetermined threshold, the apparatus 10 can automatically stop and/or reduce the flow rate provided by the pump 80 to prevent damage to the organ. In addition or alternatively, the pressure sensors 128, 138 may be used to generate warning signals to the user and/or to an appropriate controller as pressures approach the predetermined threshold. An alternate software algorithm may be employed to allow the apparatus 10 to perfuse at a preferred pressure. For example, a software algorithm may allow a doctor or clinician to select a specific pressure and vary the flow rate accordingly.

After exiting one or both of the portal flow path 120 and hepatic flow path 130, perfusate flows through the organ and returns to the basin 30 to form an organ bath.

Bypass flow path 140 may include a valve 142, and/or sensors such as oxygen sensor 144 and pH sensor 146. Preferably, the valve 142 is a pinch valve and may be of similar configuration to valves 122 and 132, but any suitable valve may be used. The oxygen sensor 144 and the pH sensor 146 may be used to determine the state of the perfusate. Preferably, the bypass flow path 140 is only used during a purging or priming process, although it may also be used during perfusion, preferably continuously, to monitor perfusate properties in real time.

The organ perfusion apparatus 10 may also include an accelerometer 150. Preferably the accelerometer 150 is a three-axis accelerometer, although multiple single axis accelerometers may be used to the same effect. The accelerometer 150 may be used to continuously or periodically monitor and/or record the state of the apparatus 10. Monitoring may include monitoring for excessive shocks as well as attitude of the apparatus 10. For example, if a pitch or a roll exceeds a pre-set alarm limit, the action of the pump 80 may be momentarily interrupted to stop the flow of perfusate until that specific condition is corrected. By implementing such monitoring, misuse or potentially inappropriate conditions of the apparatus 10 can be detected and recorded and appropriate action can be taken.

The apparatus 10 may include storage compartments for items other than the organ 20. For example, the apparatus 10 may include a document compartment 160 to store documents and/or charts related to the organ 20. Also, the apparatus 10 may include one or more sample compartment 170.

The sample compartment 170 may be configured, for example, to store fluid and/or tissue samples. The sample compartment 170 may be advantageously disposed near the coolant container 50 to provide cooling, which may be similar or equivalent to the cooling provided for the organ 20.

The apparatus 10 may include one or more tamper evident closures 180. A tamper evident closure 180 may be used to alert a user that the apparatus 10 has been opened at an unauthorized time and/or location and/or by an unauthorized person. Evidence of tampering may alert the user to perform additional testing, screening, or the like before using the organ 20 and/or the apparatus 10.

Preferably, all components of the apparatus 10 that come into contact with perfusate and/or the organ 20 are disposable and/or easily replaced. Such disposable items may be included in one or more kit or saleable package. For example, such a kit may include packaging such as plastic or shrink wrap packaging containing some or all of the components that come into contact with an organ 20 and/or perfusate. In embodiments, the tubing, filter, oxygenator and bubble trap are packaged together, and the cradle and basin are packaged individually or together, and optionally together with the tubing, filter, oxygenator and bubble trap in a manner preconfigured to be placed into a flow path arrangement of fixed-location parts in apparatus 10.

Figure 2:
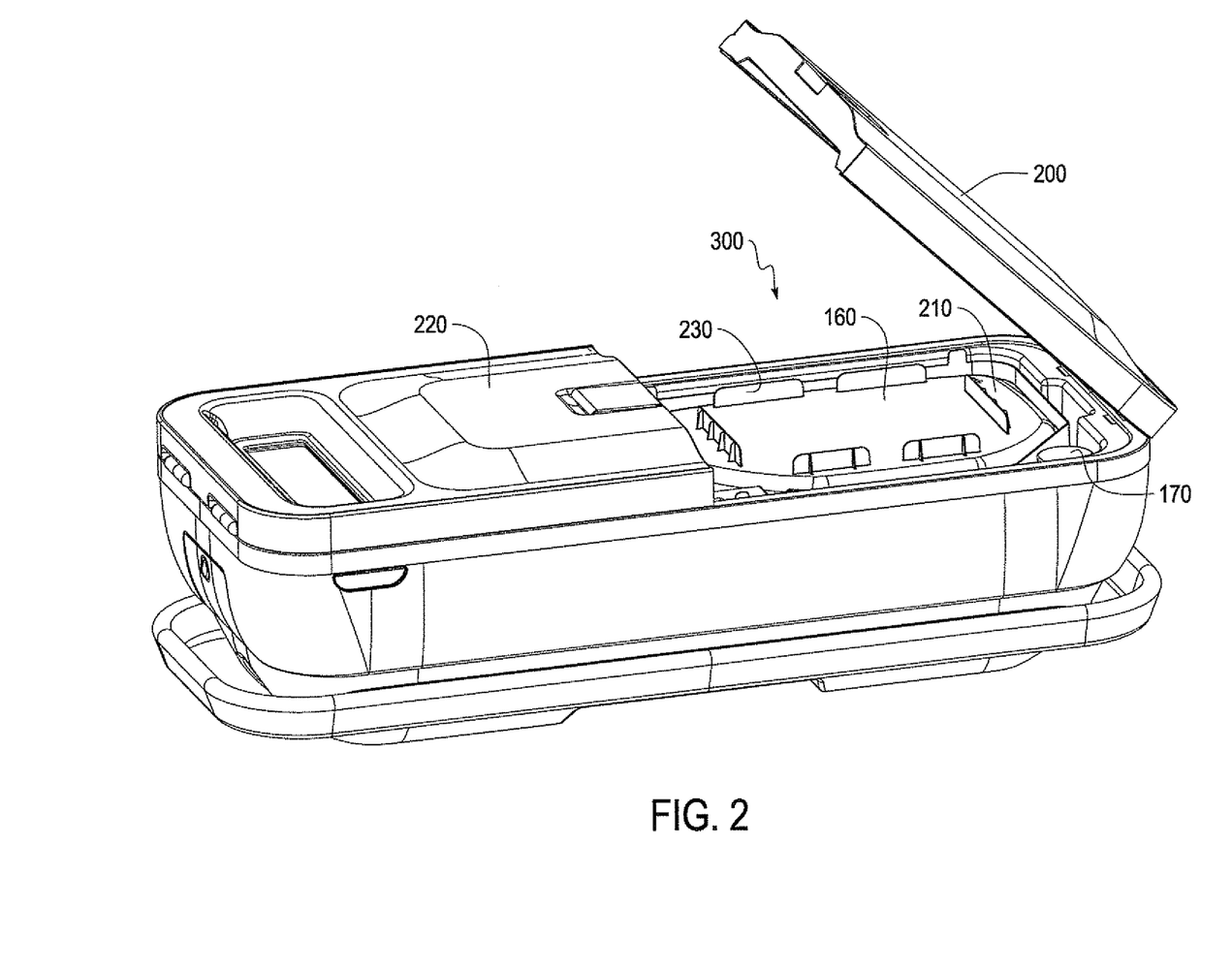
FIG. 2 illustrates an exemplary perspective view of the apparatus of FIG. 1 with a first external cover (lid) open.

FIG. 2 illustrates an exemplary perspective view of the apparatus 10 with a first external cover 200 open. A compartment, for example an internal compartment 300, may be a section of the apparatus 10 that is defined by a plurality of walls or regions that divide the apparatus 10. A compartment may be defined structurally within the apparatus 10 by physical structures or defined functionally divided by the relative location of components of the apparatus 10. Compartments may be defined as specific enclosures for a group of elements that function in relation to one another. Compartments may also be defined with respect to the position of corresponding covers.

Figure 3:
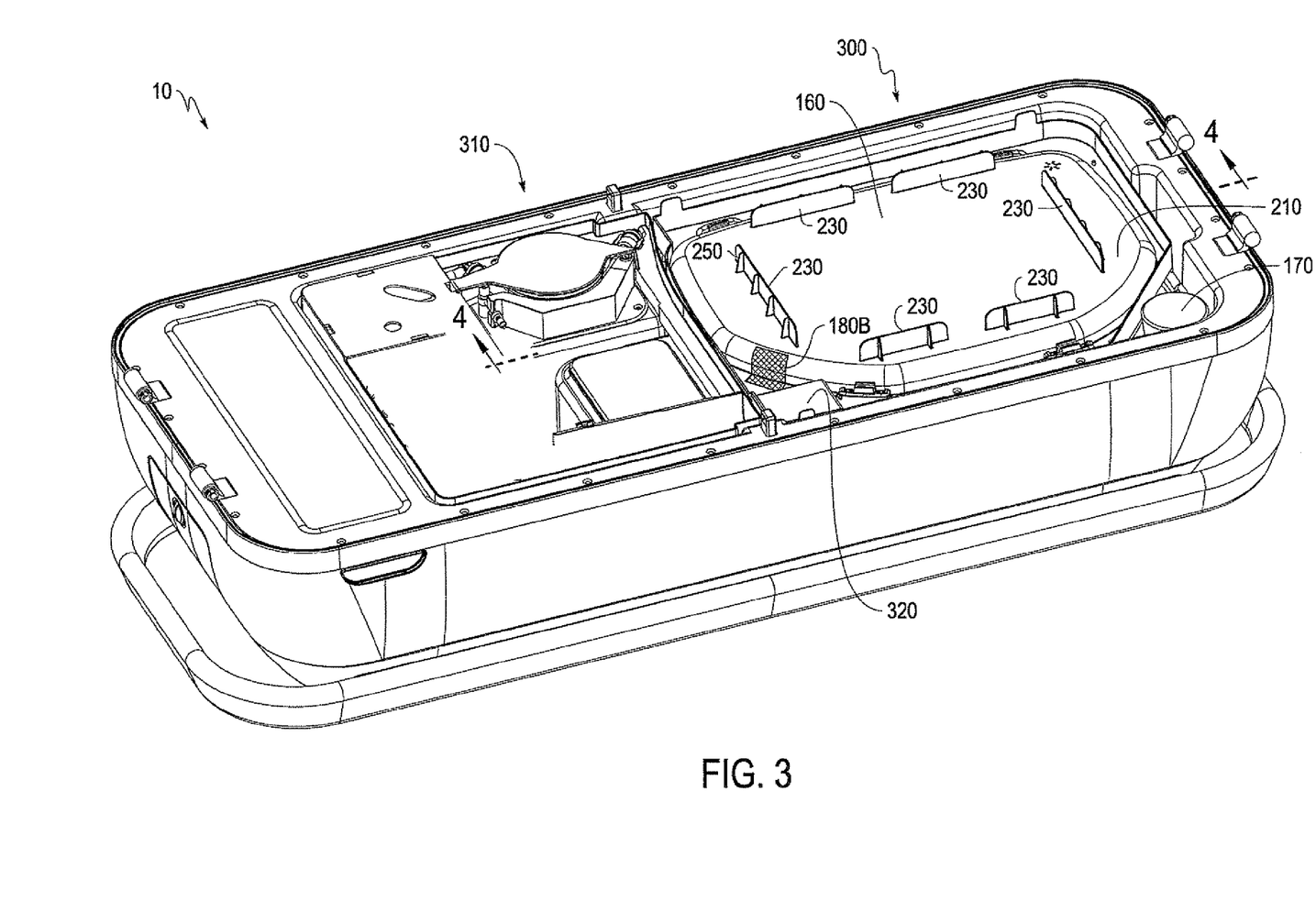
FIG. 3 illustrates an exemplary top view of the apparatus of FIG. 2 with the first and second external covers (lids) removed.

Components under specific covers may be defined as being in different compartments. For example, internal compartment 300 may be defined to be the area under the first external cover 200 and a second internal compartment 310 may be defined to be the area under the second external cover 220. FIGS. 3 and 4 illustrate that the first internal compartment 300 may include at least the basin 30, part of the cooling container 50, the cradle 60 and/or the document compartment 160. A second internal compartment 310 may include the pump 80, the bubble trap 110 and other components used to perfuse an organ 20 in the apparatus 10.

As can be particularly appreciated from FIG. 1, an overall container for organ perfusion apparatus 10 may hold numerous components in a small volume. Thus, volume for documents and/or tamper evident closures is preferably reserved and allocated in specific, efficient ways in embodiments described herein.

The document compartment 160 may be positioned between the first external cover 200 and the internal cover 210 in the first internal compartment 300. Preferably, a volume between the first external cover 200 and the internal cover 210 defines the document compartment 160. This arrangement allows documents carried by the document compartment 160 to be internally accessible only. This configuration also provides a means to limit access to the documents and/or the organ 20 to authorized personnel.

Wall portions 230 may extend substantially perpendicularly from the top surface of the internal cover 210 and/or the bottom surface of the first external cover 200. A plurality of flanges 250 may support the wall portions 230. The wall portions 230 may be integral to a cover or they may be separate parts that are connected to the cover during assembly. For example, the wall portions 230, the plurality of flanges 250 and the internal cover 210 may be injection molded as a single part. Alternatively, the wall portions 230 and the plurality of flanges 250 may be manufactured separately from the internal cover 210 and mounted on the internal cover 210 by any suitable means such as adhesives or fasteners. Thus, the document compartment 160 is defined between the first external cover 200, the internal cover 210 and the wall portions 230.

Preferably, at least four wall portions 230 are present on the internal cover 210. More wall portions 230, such as the six illustrated in FIG. 3, and various lengths and heights may be used to more effectively enclose the documents. Any or all of the illustrated wall portions 230 may be connected to form a continuous structure without one or more of the illustrated gaps. Heights of 0.1-1, such as 0.5-0.9 inches are desirable to accommodate organ documentation. The wall portions 230 may, for example, define a rectangular or square document compartment, wherein internal dimensions of the document compartment may be large enough to incorporate standard size documents. The wall portions 230 may be positioned to carry standard sizes such as A4, 8½×11", 8½×13" or any other appropriate size paper documents. For example, internal dimensions of the wall portions 230 may be at least 9×12 inches, or alternatively, 9×15 inches. Preferably, the internal dimensions of the wall portions 230 may be at least 0.9×9.8× 12.3 inches. Extra space between the document and the internal lateral dimensions of the document compartment may be advantageous for handling purposes such as effectively placing/removing the documents into/from the document compartment 160. The wall portions 230 may act as side surfaces of the document compartment 160 and the top surface of the internal cover 210 may form the bottom internal surface of the document compartment 160. The wall portions 230 may advantageously control the movement of the documents in the document compartment 160 to minimize movement of and damage to the documents during handling and transportation of the apparatus 10.

When the first external cover 200 closes the first internal compartment 300, the document compartment 160 may be closed. As a result, the bottom surface of the first external cover 200 may be the top internal surface of the document compartment 160. In this configuration, documents that may be placed in the document compartment 160 are less likely to be displaced. The bottom surface of the first external cover 200 may be in contact with or close to a top surface of the wall portions 230 to substantially close the document compartment 160. The closer these two surfaces are positioned relative to each other, the less likely it is that documents may unintentionally exit the document compartment 160 during use and/or transport.

In alternate implementations, the bottom surface of the first external cover 200 may include wall portions 230 that are in contact with or close to the top surface of the internal cover 210 to substantially close and secure documents in the document compartment 160. The wall portions 230 may be on both the first external cover 200 and the internal cover 210 in any combination.

The first external cover 200 and the second external cover 220 may be positioned over the internal compartments 300, 310, respectively, and cooperate together to close the entire apparatus 10. Preferably, the first external cover 200 and the second external cover 220 may respectively pivot around hinges at opposite ends of the internal compartments 300, 310. This configuration may allow the external covers 200, 220 to open at approximately a center of a top surface of the apparatus 10 or anywhere in between the two ends of the apparatus 10. The external covers 200, 220 may be latched closed and/or together e.g. by a latch 260. Preferably, the latch 260 may include a first latch 260A that closes and locks the first external cover 200 and a second latch 260B that closes and locks the second external cover 220. The latch 260 may include a locking mechanism to secure cover(s) in a closed position. The locking mechanism may include, for example, a spring or a taut wire to provide the necessary locking force. Preferably, the latches 260A, 260B may drive bars that that rotate to open and close locks at the sides of each of the external covers 200, 220. This configuration advantageously allows the external covers 200, 220 to cooperate in opening and closing certain portions of the apparatus 10 independently or together. Alternatively, the external covers 200, 220 could be hinged along one or more other sides of the apparatus 10 to achieve this capability. The internal cover(s) may be held in place gravitationally, by friction, by latches or the like. The internal cover(s) may be hinged, either to a surface in the compartment or to an external cover. If the internal cover is hinged to an external cover, the external cover is preferably openable 180° and wall portions preferably extend from the lower surface of the external cover so that they extend upwardly when the external cover is fully opened.

The two internal compartments 300, 310 and the corresponding external covers 200, 220 may be separate and independent from each other such that when the first external cover 200 is closed and the second external cover 220 is open or closed, the document compartment 160 and/or the organ 20 may not be accessible. This configuration advantageously isolates a portion of the apparatus 10 to be open or closed while maintaining security of the organ 20 and/or documents in the document compartment 160. In another configuration, the document compartment 160 may be under the second external cover 220 and enclosed in the second internal compartment 310.

FIG. 4 illustrates that a basin cover 240 may close and seal the basin 30 to maintain a sterile environment for an organ before, during and/or after organ transport. The basin cover 240 may also advantageously close and seal the basin 30 during and/or after hypothermic machine perfusion. Preferably, a flange of the basin cover 240 may be positioned adjacent to an upper surface of the cradle 60 to minimize movement of the cradle 60 during transport of the apparatus 10.

The basin 30 and/or basin cover 240 may use a sealing mechanism, for example an o-ring and an o-ring groove, to help preserve the sterile environment. This configuration may also prevent fluid egress from the basin 30. The first internal compartment 300 and/or internal cover 210 may also be configured with a sealing mechanism to provide a secondary or back up seal. The internal cover 210 may also be used to help preserve the sterile environment for the organ 20 and provide added security. The sealing capacity of both covers 210, 240 may improve the reliability of maintaining the sterile environment if one of the sealing mechanisms fails.

The external covers 200, 220 may also use a similar sealing mechanism to seal the internal compartments 300, 310, respectively, from contamination and fluid egress. Since the document compartment 160 may preferably be located between the first external cover 200 and the internal cover 210, the document compartment 160 is effectively sealed from external contamination and from perfusate and/or other substances in the first internal compartment 300. This configuration advantageously protects the documents in the document compartment 160.

Exemplary implementations may incorporate tamper evident closures 180. For example, it may be beneficial to know if any of the documents in the document compartment 160, the perfusion circuit and/or the organ 20 have been accessed prior to using the organ 20. After items such as the cradle 60 holding the organ 20, the perfusion circuit and/or the documents in the document compartment 160 are placed within the apparatus 10, various tamper evident closures 180 may be used to protect these items. The following locations of the tamper evident closures 180 are exemplary, and one of ordinary skill would readily understand that other locations and/or quantities are contemplated by the broad inventive principles discussed herein.

Figure 5A:
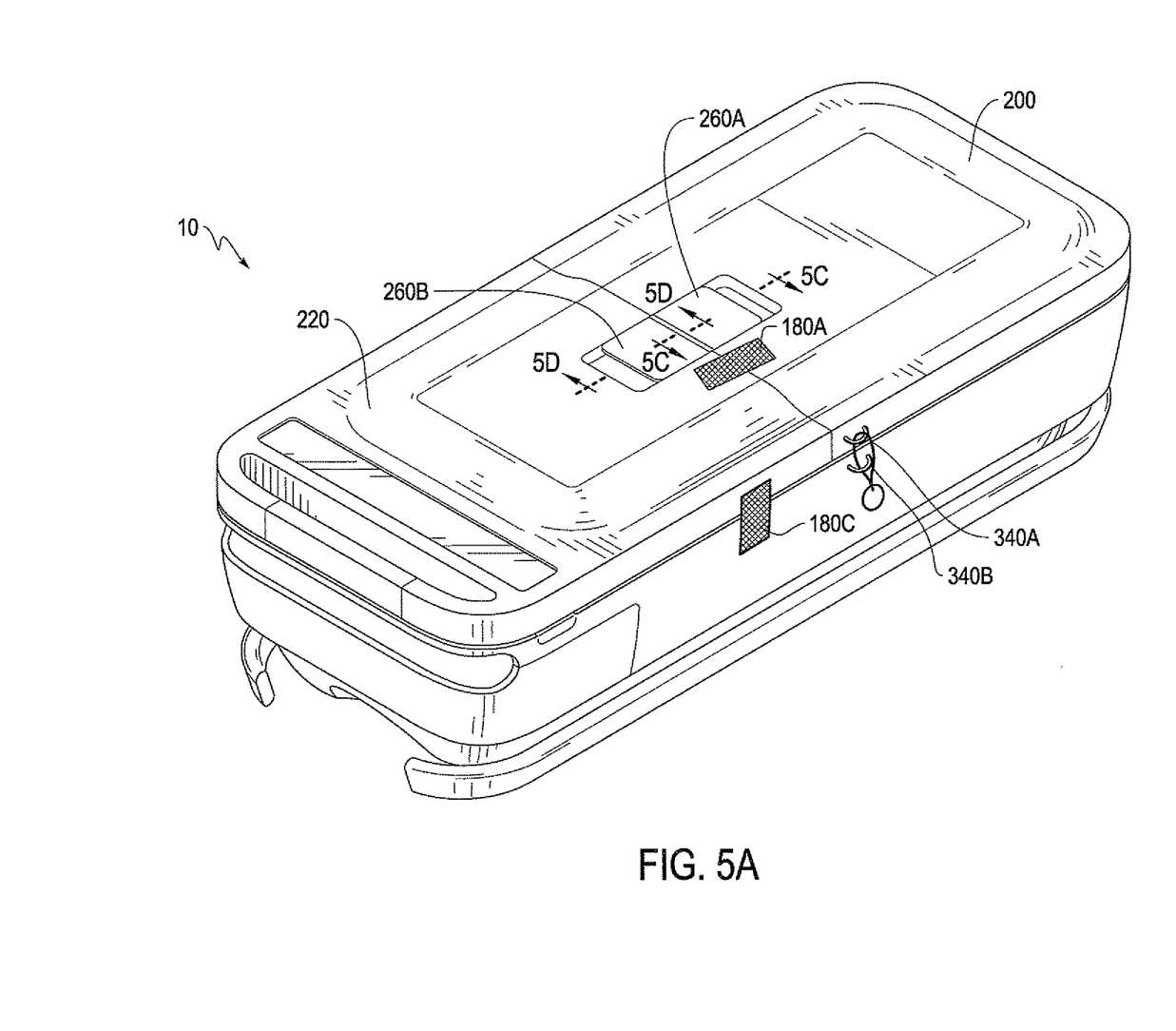
FIG. 5A illustrates an exemplary perspective view of a perfusion apparatus in the closed position.

FIG. 5A illustrates tamper evident closure 180A for the first external cover 200 of the first internal compartment 300. The tamper evident closure 180A may indicate whether the first external cover 200 has been opened. The tamper evident closure 180A may be on the first external cover 200 and another surface that is not the first external cover 200 so that the tamper evident closure 180A can be broken, removed or otherwise indicate that the first external cover 200 has been opened. FIG. 5A illustrates, for example, that the tamper evident closure 180A may be applied on the first external cover 200 and the second external cover 220. Alternatively or in addition, for example, the tamper evident closure 180A may be applied on the first external cover 200 and the body of the apparatus 10, for example at 340A and 340B.

FIG. 3 illustrates a second tamper evident closure 180E for the internal cover 210. The second tamper evident closure 180B may indicate whether the internal cover 210 has been opened. The second tamper evident closure 180B may be on the internal cover 210 and another surface that is not the internal cover 210 so that the second tamper evident closure 180B can be broken, removed or otherwise indicate that the internal cover 210 has been opened. FIG. 3 illustrates, for example, that the second tamper evident closure 180B may be applied on the internal cover 210 and a surface in the first internal compartment 300. Alternatively, the second tamper evident closure 180B may be applied elsewhere on the internal cover 210 and the body of the apparatus 10. Preferably, the second tamper evident closure 180B is not damaged when the first external cover 200 is opened or closed. Additional tamper evident closures 180 may be applied to the basin cover 240, the basin 30 and/or the cradle 60 in a similar manner as discussed above to achieve increased security and protection.

FIG. 5A illustrates a third tamper evident closure 180C for the second external cover 220 of the second internal compartment 310. The third tamper evident closure 180C may indicate whether the second external cover 220 has been opened. The third tamper evident closure 180C may be on the second external cover 220 and another surface that is not the second external cover 220 so that the third tamper evident closure 180C can be broken, removed or otherwise indicate that the second external cover 220 has been opened. FIG. 5A illustrates, for example, that the third tamper evident closure 180C may be applied on the second external cover 220 and the body of the apparatus 10. The first tamper evident closure 180A may act as a tamper evident closure 180 for the first external cover 200 as well as for the second external cover 220 if the first tamper evident closure 180A is applied on surfaces of the external covers 200 and 220.

If any of the tamper evident closures 180 indicate that any of cover(s) 200, 210, 220 have been opened, the doctor or clinician may be able to diagnose potential problems with the documents and/or the organ 20, conduct additional testing on the organ 20 prior to use, and/or refuse to use the organ altogether. Thus, the tamper evident closures 180 provide added protection and security during the transport and/or storage of the organ 20 and the associated documents to improve the safety, efficiency and likelihood of success of use of the organ 20.

The tamper evident closures 180 may be of a frangible material and be activated by being connected between any cover and another part of the apparatus 10. The tamper evident closures 180 or apparatus 10 may alternatively or additionally include one or more electronic sensor 320 that provides information that one or more of cover(s) 200, 210, 220 have been opened. The electronic sensor(s) 320 may be configured to detect a cover being opened. For example, a mechanically actuated switch or a Hall-effect sensor may be used. This information may help the doctor or clinician determine when and/or for how long one or more cover has been opened. Information from the electronic sensor(s) 320 can be used to determine whether further tests are needed to diagnose the health and viability of the organ 20. Electronic sensor(s) 320 may be used in combination with other types of tamper evident closures for redundancy.

FIG. 5A illustrates various types of tamper evident closures 180. The following types of tamper evident closures 180 are exemplary, and one of ordinary skill would readily understand that other types are contemplated and implemented by the broad inventive principles discussed herein.

A tamper evident closure 180 may include a first loop 340A and a second loop 340B linked together by an item such as a frangible connector to secure the first external cover 200 in a closed position. The first loop 340A may be attached to an outer surface of the apparatus 10 while the second loop 340B may be attached to the outer surface of the first external cover 200. A frangible connector may be affixed securely to the first and second loops 340A, 340B after the first external cover 200 is closed. A broken or removed connector indicates that the first external cover 200 has been opened. This configuration advantageously provides a tamper evident closure 180 to the apparatus 10 in a simple, cost effective and reliable manner. Alternatively, the first loop 340A may be attached to the outer surface of the second external cover 220. In this configuration, a broken or removed connector indicates that at least one of the first and second external covers 200, 220 has been opened.

Figure 5B:
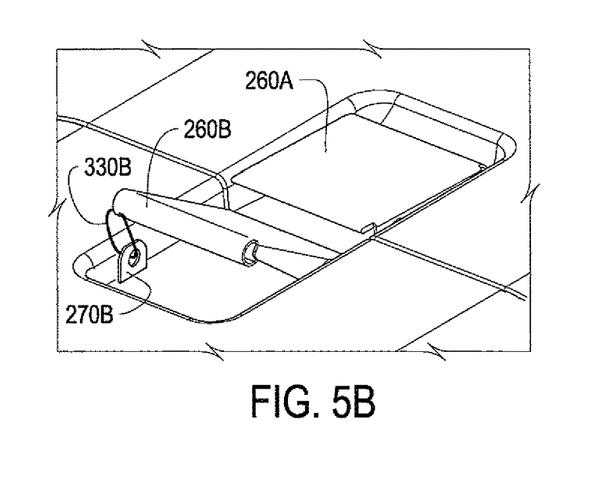
FIG. 5B illustrates an exemplary perspective view of a first and second latch of FIG. 5A where the first latch is in a closed position and the second latch is in an open position.
Figure 5C:
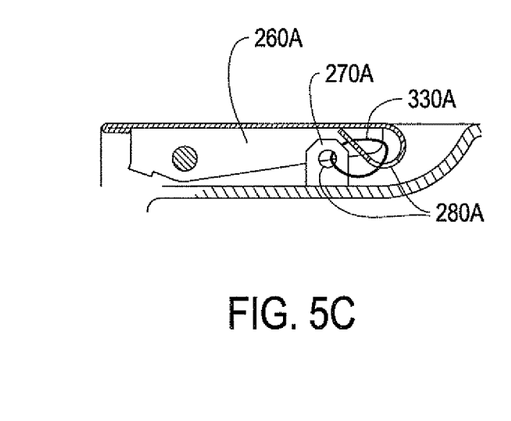
FIG. 5C illustrates an exemplary cross-sectional view, taken along the line 5C-5C in FIG. 5A, of the first latch in the closed position.
Figure 5D:
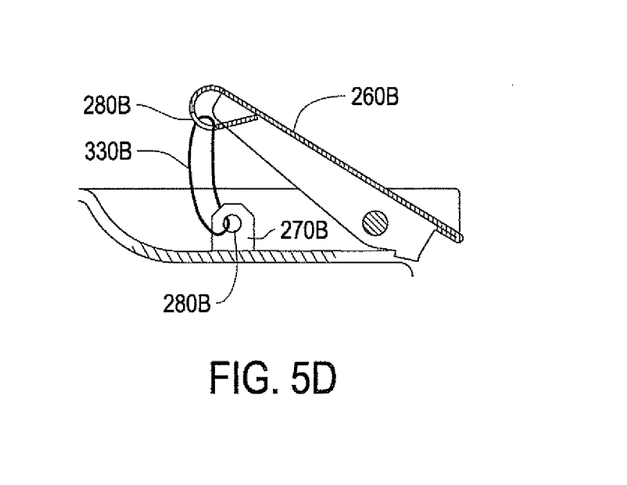
FIG. 5D illustrates an exemplary cross-sectional view, taken along the line 5D-5D in FIG. 5A, of the second latch in the open position.

FIGS. 5B, 5C and 5D illustrate a configuration of a tamper evident closure 180 where a frangible connector, such as a zip tie loop 330A, may be affixed securely to a hole or hook 280A of the first latch 260A and to a hole or hook 280A in a latch plate 270A. The latch plate 270A may be secured in a recess of the first external cover 200 where the first latch 260A is located. A similar configuration may be employed for the second latch 260B, latch plate 270B, zip tie loop 330B and respective holes or hooks 280B. As illustrated in FIGS. 5C and 5D, latch plates 270A, 270B may be arranged at alternating sides of the latches 260A, 260B, respectively. A broken or removed zip tie loop 330A, 330B indicates that the external covers 200, 220, respectively, have been opened. This preferred configuration advantageously provides a tamper evident closure 180 to the apparatus 10 in a concealed yet simple and reliable manner.

A tamper evident closure 180 may be a label such as a security label or a label with a bar code. The first tamper evident closure 180A may be applied across a surface of the first external cover 200 and a surface that is not part of the first external cover 200 while the first external cover 200 is in a closed position. As discussed above, the tamper evident closures 180 can be positioned at various locations. The security label and/or the bar code may be created so that a duplicate cannot be easily made. A torn or removed label may indicate that cover(s) 200, 210, 220 has been opened. A tamper evident closure may include coded information such as in a bar code or magnetic strip. The doctor or clinician may be able to confirm the information in the bar code of the tamper evident closure 180 to determine that the organ 20 and the documents are in their original state. The unique information may prevent a closure from being duplicated and applied after an unauthorized person has opened the apparatus 10.

It should be appreciated that various features disclosed above and other features and functions, or alternatives thereof, may be desirably combined into many other different devices. Also, various presently and unforeseen or unanticipated alternatives, modifications, variations or improvements therein may be subsequently made by those skilled in the art which are also intended to be encompassed by this disclosure.

What is claimed is:

1. A perfusion apparatus comprising:
a perfusion circuit configured to perfuse an organ or tissue;
an organ compartment in which the organ or tissue may be supported during perfusion by the perfusion apparatus;
a first external cover configured to close the perfusion apparatus in a closed state;
an internal cover separate from the first external cover such that movement of the first external cover does not cause corresponding movement of the internal cover, the internal cover being between the organ compartment and the first external cover in the closed state of the first external cover; and
a rigid wall portion extending, in the closed state of the first external cover, substantially perpendicularly between the internal cover and the first external cover to define a document compartment in a volume between the internal cover, the first external cover and the wall portion,
wherein a longitudinal plane of the internal cover does not intersect a longitudinal plane of the first external cover when the first external cover is in the closed state, and
wherein the rigid wall portion is fixed to the internal cover so that the rigid wall portion correspondingly moves with the internal cover.

2. The perfusion apparatus of claim 1, wherein
the wall portion extends from the internal cover, and
a bottom surface of the first external cover is adjacent to a top surface of the wall portion to substantially enclose the document compartment.

3. The perfusion apparatus of claim 1, wherein the wall portion comprises four wall portions that define a rectangular document compartment.

4. The perfusion apparatus of claim 3, wherein internal dimensions of the document compartment are at least 0.5×9×12 inches.

5. The perfusion apparatus of claim 3, wherein internal dimensions of the document compartment are at least 0.9×9.8×12.3 inches.

6. The perfusion apparatus of claim 1, further comprising a second external cover configured to close the perfusion apparatus in cooperation with the first external cover, the second external cover being arranged such that the document compartment is not open when the first external cover is closed and the second external cover is either open or closed.

7. The perfusion apparatus of claim 1, comprising:
a tamper evident seal configured to indicate whether the first external cover has been opened after the tamper evident seal has been activated.

8. The perfusion apparatus of claim 1, comprising:
a tamper evident seal configured to indicate whether the internal cover has been opened after the tamper evident seal has been activated.

9. The perfusion apparatus of claim 6, comprising:
a tamper evident seal configured to indicate whether the second external cover has been opened after the tamper evident seal has been activated.

10. The perfusion apparatus of claim 1, further comprising:
an electronic sensor that is configured to provide information indicating whether or not the first external cover has been opened.

11. The perfusion apparatus of claim 7, comprising:
a first loop that is attached on an outer surface of the perfusion apparatus other than an outer surface of the first external cover; and
a second loop that is attached on the outer surface of the first external cover, wherein
the tamper evident seal engages the first and second loops to activate the tamper evident seal.

12. The perfusion apparatus of claim 7, wherein the tamper evident seal is a label.

13. The perfusion apparatus of claim 7, wherein the tamper evident seal includes a bar code.

14. The perfusion apparatus of claim 1, wherein in the closed state of the first external cover, the rigid wall portion extends from a surface of the internal cover facing the first external cover.

15. The perfusion apparatus of claim 1, wherein:
in the closed state, the first external cover covers an opening in the perfusion apparatus; and
in an opened state of the first external cover, the document compartment is accessible to a user of the perfusion apparatus by way of the opening.

16. A method of preparing an organ or tissue and an associated document for transportation or storage, the method comprising:
placing the organ or tissue in an organ compartment in a perfusion apparatus having a first external cover configured to close the perfusion apparatus in a closed state;
placing the document in a document compartment of the perfusion apparatus that is under the first external cover when the first external cover is closed, the document compartment being defined by a volume between the first external cover, a rigid wall portion, and an internal cover separate from the first external cover such that movement of the first external cover does not cause corresponding movement of the internal cover; and
closing the first external cover so that the internal cover is between the organ compartment and the first external cover, the rigid wall portion extends substantially perpendicularly between the internal cover and the first external cover, and a longitudinal plane of the internal cover does not intersect a longitudinal plane of the first external cover,
wherein the rigid wall portion is fixed to the internal cover so that the rigid wall portion correspondingly moves with the internal cover.

17. The method of claim 16, further comprising:
activating a first tamper-evident seal after placing the organ or tissue and the document in the perfusion apparatus and closing the first external cover, wherein the first tamper-evident seal indicates whether or not the first external cover has been opened after the first tamper-evident seal has been activated.

18. The method of claim 17, further comprising:
activating a second tamper-evident seal after placing the organ or tissue in the compartment in the perfusion apparatus and closing the organ compartment with the internal cover, wherein the second tamper-evident seal indicates whether or not the internal cover has been opened after the second tamper-evident seal has been activated.

19. The method of claim 18, further comprising:
closing the perfusion apparatus with a second external cover in cooperation with the first external cover; and
activating a third tamper-evident seal after closing the second external cover, wherein the third tamper-evident seal indicates whether or not the second external cover has been opened after the third tamper-evident seal has been activated.

20. The method of claim 17, wherein the first tamper-evident seal comprises a frangible material and is activated by being connected between the first external cover and another part of the perfusion apparatus.

21. The method of claim 17, wherein the perfusion apparatus comprises an electronic sensor.

22. The method of claim 16, further comprising:
perfusing the organ or tissue in the organ compartment while the first external cover is closed.

23. The method of claim 16, wherein when the first external cover is closed, the rigid wall portion extends from a surface of the internal cover facing the first external cover.

24. The method of claim 16, wherein:
when the first external cover is closed, the first external cover covers an opening in the perfusion apparatus; and
when the first external cover is opened, the document compartment is accessible to a user of the perfusion apparatus by way of the opening.

* * * * *